US00PP21025P2

(12) United States Plant Patent

Klemm et al.

(10) Patent No.: US PP21,025 P2

(45) Date of Patent: May 25, 2010

(54) *NEMESIA* PLANT NAMED 'KLENH08446'

(50) Latin Name: *Nemesia hybrida*
Varietal Denomination: KLENH08446

(75) Inventors: Nils Klemm, Stuttgart (DE); Katinka Wilde, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/383,913

(22) Filed: Mar. 30, 2009

(51) Int. Cl.
*A01H 5/00* (2006.01)

(52) U.S. Cl. ..... Plt./458

(58) Field of Classification Search ..... Plt./458
See application file for complete search history.

*Primary Examiner*—Annette H Para
(74) *Attorney, Agent, or Firm*—Jondle & Associates, P.C.

(57) ABSTRACT

A new cultivar of *Nemesia* named 'KLENH08446' particularly characterized by light-purple flowers with large, dark-purple eyes and red-purple margins, an upright plant habit with a medium-vigorous growth habit and a long flowering period, is disclosed.

1 Drawing Sheet

Genus and species: *Nemesia hybrida.*
Variety denomination: 'KLENH08446'.

BACKGROUND OF THE NEW PLANT

The present invention comprises a new and distinct cultivar of *Nemesia,* botanically known as *Nemesia hybrida*, and hereinafter referred to by the cultivar name 'KLENH08446'. 'KLENH08446' originated from a controlled cross made in June 2005 in Stuttgart, Germany between the proprietary female *Nemesia* plant 'NH 05 105' (unpatented) and the proprietary male *Nemesia* plant 'NH 05 108' (unpatented). A single plant selection was subsequently chosen for further evaluation and for asexual propagation.

The new cultivar was first propagated in September 2006 in Stuttgart, Germany and has been asexually reproduced repeatedly by vegetative cuttings and in-vitro propagation in Stuttgart, Germany for about a two and one-half year period (about 6 generations). 'KLENH08446' has been found to retain its distinctive characteristics through successive asexual propagations.

Plant Breeders Rights have not been applied for this cultivar. 'KLENH08446' has not been made publicly available more than one year prior to the filing date of the instant application.

SUMMARY OF THE INVENTION

The following are the most outstanding and distinguishing characteristics of this new cultivar when grown under normal commercial practices in a greenhouse in Stuttgart, Germany.

1. Light-purple flowers with large, dark-purple eyes and red-purple margins;
2. An upright plant habit with a medium-vigorous growth habit; and
3. A long flowering period.

DESCRIPTION OF THE PHOTOGRAPH

This new *Nemesia* plant is illustrated by the accompanying photograph which shows a close-up of the mature flowers, buds and foliage; the colors shown are as true as can be reasonably obtained by conventional photographic procedures. The photograph is of a plant about 18-weeks old and grown from rooted cuttings in 10.5 cm pots in a greenhouse (glasshouse) in Stuttgart, Germany in spring 2008 under conditions which approximate those generally used in commercial practice.

DESCRIPTION OF THE NEW CULTIVAR

The following detailed descriptions set forth the distinctive characteristics of 'KLENH08446'. The data which define these characteristics were collected from asexual reproductions carried out in Stuttgart, Germany. The plant history was taken on 18-week old plants in 10.5 cm pots that were pinched once after 10 weeks and grown in a greenhouse in spring 2008. The color readings were determined under natural light. Color references are to the RHS Colour Chart of The Royal Horticultural Society of London (RHS) (2001).

DESCRIPTION OF THE NEW PLANT

Classification:
- *Family.*—*Scrophulariaceae.*
- *Genus and species.*—*Nemesia hybrida.*
- *Common name.*—*Nemesia.*

Parentage:
- *Female parent.*—The proprietary female *Nemesia* plant 'NH 05 105' (unpatented).
- *Male parent.*—The proprietary male *Nemesia* plant 'NH 05 108' (unpatented).

Plant:
- *Habit or form.*—Upright.
- *Vigor.*—Medium.
- *Height* (*measured from the top of the soil, including flowers*).—About 23.0 cm.
- *Spread/width* (*horizontal plant diameter, including flowers*).—About 20.0 cm.
- *Life cycle.*—Annual.
- *Time to produce a rooted cutting.*—3 to 4 weeks.
- *Time to produce a finished flowering plant.*—6 weeks.
- *Flowering season.*—Spring.

*Root description.*—Filiform, pale-colored roots with root hairs.
*Rooting habit.*—Medium root density and freely branching.
*Temperature tolerances.*—5° C. to 35° C.
*Environmental conditions for plant growth and performance.*—Tolerates wind and rain and has good outdoor performance.

Branches:
*Type.*—Mostly basal branching.
*Quantity per plant.*—About 7.
*Length.*—About 22.0 cm.
*Diameter.*—About 0.4 cm.
*Internode length.*—About 2.0 cm.
*Strength of branches.*—Robust (strong).
*Color.*—RHS 144A.
*Texture.*—Smooth (no pubescence).
*Stem anthocyanin.*—Absent.
*Branch pubescence.*—Absent.

Leaves:
*Arrangement.*—Opposite and sessile.
*Shape.*—Lanceolate.
*Apex.*—Cuspidate.
*Base.*—Obtuse.
*Margin.*—Serrate.
*Length.*—2.7 cm to 4.0 cm.
*Width.*—1.7 cm.
*Color* (*both mature and immature leaves*).—Upper surface: RHS 144A. Lower surface: RHS 144B.
*Variegation.*—Absent.
*Surface texture* (*both surfaces*).—Smooth (no pubescence).
*Venation pattern.*—Pinnate.
*Venation color* (*both mature and immature leaves*).—Upper surface: RHS 144A. Lower surface: RHS 144B.
*Petioles.*—Absent.

Flower bud:
*Quantity per inflorescence.*—2 to 5.
*Shape.*—Obovate.
*Surface texture.*—Smooth.
*Diameter.*—0.3 cm to 0.5 cm.
*Length.*—0.4 cm to 0.9 cm.
*Color* (*at tight bud*).—RHS 150D.

Inflorescence:
*Inflorescence type.*—Raceme.
*Lastingness of inflorescence on the plant.*—About 7 days.
*Quantity of flowers per inflorescence.*—2 to 6.
*Inflorescence length.*—About 9.0 cm.
*Inflorescence diameter.*—About 1.5 cm not including the flowers and about 3.0 cm including the flowers.
*Flower diameter.*—About 1.6 cm.
*Flower depth* (*including nectar spur*).—About 1.0 cm.
*Nectar spur length.*—About 0.4 cm.
*Fragrance.*—Strong.
*Self-cleaning or persistent.*—Self-cleaning.

Petals:
*Arrangement and shape.*—Zygomorphic; flowers are arranged on terminal racemes; four petals are fused at the base and the fifth lower petal is modified into a large lip.
*Quantity per flower.*—5.
*Length* (*both the upper and lower lips*).—About 2.5 cm.
*Width* (*both the upper and lower lips*).—About 1.6 cm.
*Apex.*—Lobate/obtuse.
*Margin.*—Entire.
*Color.*—Upper lip: Young flowers are RHS 55D and mature flowers are RHS 78D with RHS 83B eyes; young and mature flowers also have an RHS 71A border. Lower lip: RHS 78D.
*Texture* (*both surfaces of upper and lower lips*).—Smooth (no pubescence).
*Nectar spur color.*—RHS 194D.
*Nectar guide color.*—RHS 1A.
*Spur length.*—About 0.3 cm.
*Spur diameter at the base.*—About 0.5 cm.
*Spur diameter at the tip.*—About 0.1 cm.
*Spur texture.*—Smooth.

Calyx:
*Shape and arrangement.*—Star-shaped with 5 sepals fused at the base.
*Sepals.*—Quantity: 5. Apex: Cuspidate. Base: Fused. Margin: Entire. Color (both surfaces): RHS 139B. Length: About 0.7 cm. Diameter: About 0.7 cm. Surface texture (both surfaces): Pubescent.

Pedicel:
*Length.*—About 0.8 cm.
*Diameter.*—About 0.1 cm.
*Color.*—RHS 139C.
*Surface texture.*—Pubescent.

Peduncle:
*Length.*—About 2.5 cm.
*Diameter.*—About 0.2 cm.
*Color.*—RHS 141C.
*Surface texture.*—Smooth (not pubescent).

Reproductive organs:
*Stamens.*—Number per flower: 4. Length: About 0.3 cm. Filament color: RHS 196D. Filament length: About 0.2 cm. Filament diameter: About 0.1 cm. Anther color: RHS 22B. Anther length: About 0.1 cm. Pollen amount: Moderate. Pollen color: RHS 22B.
*Pistil.*—Pistil number: 1. Pistil length: About 0.3 cm. Stigma color: RHS 155D. Stigma length: Not available; not distinguishable from style. Style length: About 0.1 cm. Style color: RHS 155D.
*Ovary.*—Shape: Ovate. Color: RHS 145B.

Fruit and seed set: None observed.
Disease and insect resistance: None observed.

COMPARISON WITH PARENTAL AND COMMERCIAL CULTIVARS

'KLENH08446' differs from the proprietary female *Nemesia* plant 'NH 05 105' (unpatented) in that 'KLENH08446' has light-purple flowers with darker purple eyes and red-purple margins, while 'NH 05 105' has dark-violet flowers. Additionally, 'KLENH08446' has better and more branching than 'NH 05 105'.

'KLENH08446' differs from the proprietary male *Nemesia* plant 'NH 05 108' in that 'KLENH08446' has smaller flowers and a less vigorous growth habit than 'NH 05 108'.

'KLENH08446' differs from the commercial comparison variety 'KLENH06442' (unpatented) in that 'KLENH08446' has flowers with dark-purple eyes, while 'KLENH06442' has flowers without eyes. Additionally, 'KLENH08446' has a less vigorous growth habit than 'KLENH06442'.

I claim:

1. A new and distinct cultivar of *Nemesia* plant named 'KLENH08446' as shown and described herein.

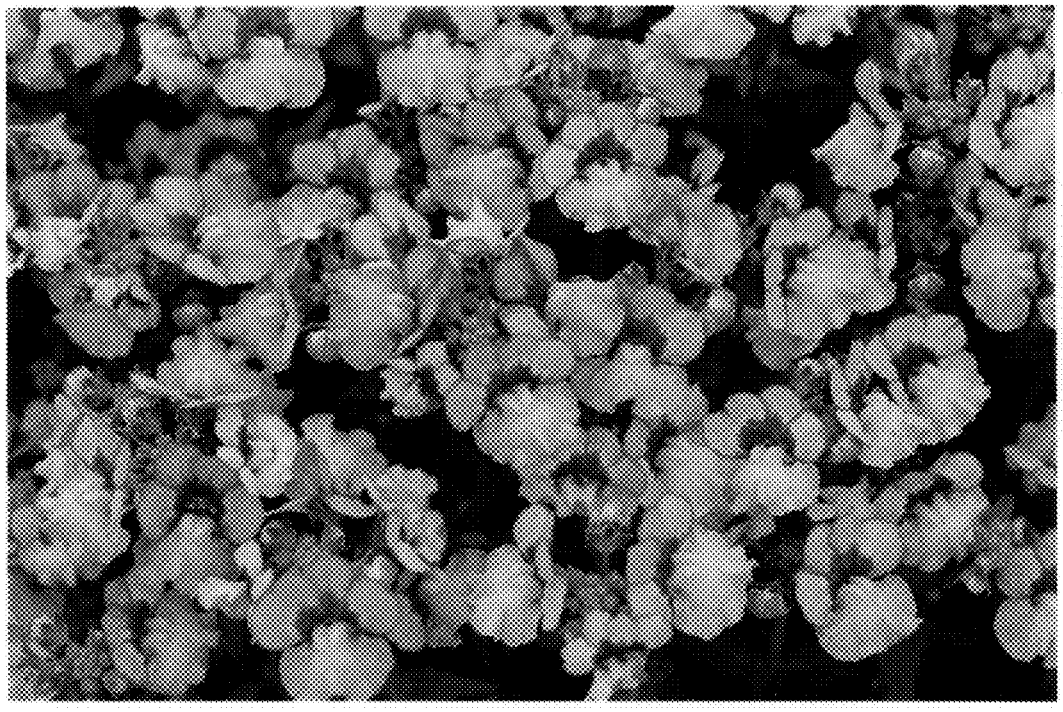

* * * * *